(12) United States Patent
Bessler et al.

(10) Patent No.: US 7,837,645 B2
(45) Date of Patent: *Nov. 23, 2010

(54) ENDOSCOPIC GASTRIC BYPASS

(75) Inventors: Marc Bessler, Teaneck, NJ (US); John D. Allendorf, Sleepy Hollow, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 797 days.

This patent is subject to a terminal disclaimer.

(21) Appl. No.: 11/681,821

(22) Filed: Mar. 5, 2007

(65) Prior Publication Data

US 2008/0033574 A1    Feb. 7, 2008

Related U.S. Application Data

(63) Continuation of application No. 10/229,400, filed on Aug. 26, 2002, now Pat. No. 7,211,114.

(51) Int. Cl.
*A61M 5/00* (2006.01)
*A61F 2/04* (2006.01)
*A61F 2/02* (2006.01)
*A61F 11/00* (2006.01)
*A61B 17/00* (2006.01)

(52) U.S. Cl. ............................. 604/8; 604/9; 623/23.65; 623/23.68; 623/23.7; 623/23.71; 623/23.75; 606/108; 606/153; 606/154; 606/155; 606/157

(58) Field of Classification Search ...................... 604/8, 604/9, 915, 920; 606/108, 153, 154, 155, 606/156, 157; 623/23.65, 23.68, 23.7, 23.71, 623/23.75, FOR. 108, 926

See application file for complete search history.

(56) References Cited

U.S. PATENT DOCUMENTS

| 4,134,405 | A |   | 1/1979  | Smit                |
|-----------|---|---|---------|---------------------|
| 4,315,509 | A | * | 2/1982  | Smit ........... 606/108 |
| 4,501,264 | A |   | 2/1985  | Rockey              |
| 4,846,836 | A |   | 7/1989  | Reich               |
| 5,085,629 | A |   | 2/1992  | Goldberg et al.     |
| 5,180,364 | A |   | 1/1993  | Ginsburg            |
| 5,306,300 | A | * | 4/1994  | Berry ........... 623/23.64 |
| RE35,849  | E |   | 7/1998  | Soehendra           |
| 5,820,584 | A |   | 10/1998 | Crabb               |
| 5,824,071 | A |   | 10/1998 | Nelson et al.       |
| 6,197,022 | B1|   | 3/2001  | Baker               |
| 6,254,642 | B1|   | 7/2001  | Taylor              |
| 6,261,305 | B1|   | 7/2001  | Marotta et al.      |

(Continued)

FOREIGN PATENT DOCUMENTS

| WO | WO 2004/017863 | 3/2004  |
|----|----------------|---------|
| WO | WO 2007/121028 | 10/2007 |
| WO | WO 2008/116207 | 9/2008  |

*Primary Examiner*—Leslie R Deak
*Assistant Examiner*—Adam Marcetich
(74) *Attorney, Agent, or Firm*—Miles & Stockbridge P.C.; Mark A. Catan, Esq.; Michael A. Minter, Esq.

(57) ABSTRACT

An endoscopic device separates ingested food from gastric fluids or gastric fluids and digestive enzymes, to treat obesity. In a particular embodiment a gastric bypass stent comprises a tubular member and two or more stent members defining a lumen. The tubular member has a substantially liquid impervious coating or covering and one or more lateral openings to permit one-way liquid flow.

22 Claims, 2 Drawing Sheets

U.S. PATENT DOCUMENTS

| | | |
|---|---|---|
| 6,264,700 B1 | 7/2001 | Kilcoyne et al. |
| 6,302,917 B1 | 10/2001 | Dua et al. |
| 6,675,809 B2 | 1/2004 | Stack et al. |
| 6,845,776 B2 | 1/2005 | Stack et al. |
| 7,037,344 B2 | 5/2006 | Kagan et al. |
| 7,211,114 B2 | 5/2007 | Bessler et |
| 7,229,428 B2 | 6/2007 | Gannoe et al. |
| 7,335,210 B2 * | 2/2008 | Smit ........................ 606/108 |
| 2002/0062146 A1 | 5/2002 | Makower et al. |
| 2003/0065359 A1 | 4/2003 | Weller et al. |
| 2003/0199991 A1 | 10/2003 | Stack et al. |
| 2004/0039452 A1 | 2/2004 | Bessler |
| 2004/0087977 A1 | 5/2004 | Nolan et al. |
| 2004/0092892 A1 | 5/2004 | Kagan et al. |
| 2004/0117031 A1 | 6/2004 | Stack et al. |
| 2004/0138761 A1 | 7/2004 | Stack et al. |
| 2004/0249362 A1 * | 12/2004 | Levine et al. ............... 604/523 |
| 2005/0043817 A1 * | 2/2005 | McKenna et al. ......... 623/23.65 |
| 2005/0049718 A1 | 3/2005 | Dann et al. |
| 2005/0085923 A1 | 4/2005 | Levine et al. |
| 2005/0096673 A1 | 5/2005 | Stack et al. |
| 2005/0125075 A1 | 6/2005 | Meade et al. |
| 2005/0251159 A1 | 11/2005 | Ewers et al. |
| 2005/0256587 A1 | 11/2005 | Egan |
| 2005/0277963 A1 | 12/2005 | Fields |
| 2006/0135963 A1 | 6/2006 | Kick et al. |
| 2006/0157067 A1 | 7/2006 | Saadat et al. |
| 2006/0217762 A1 | 9/2006 | Maahs et al. |
| 2006/0259061 A1 | 11/2006 | Kick et al. |
| 2006/0265011 A1 | 11/2006 | Bonutti |
| 2008/0009888 A1 | 1/2008 | Ewers et al. |
| 2008/0228126 A1 | 9/2008 | Bessler |

* cited by examiner

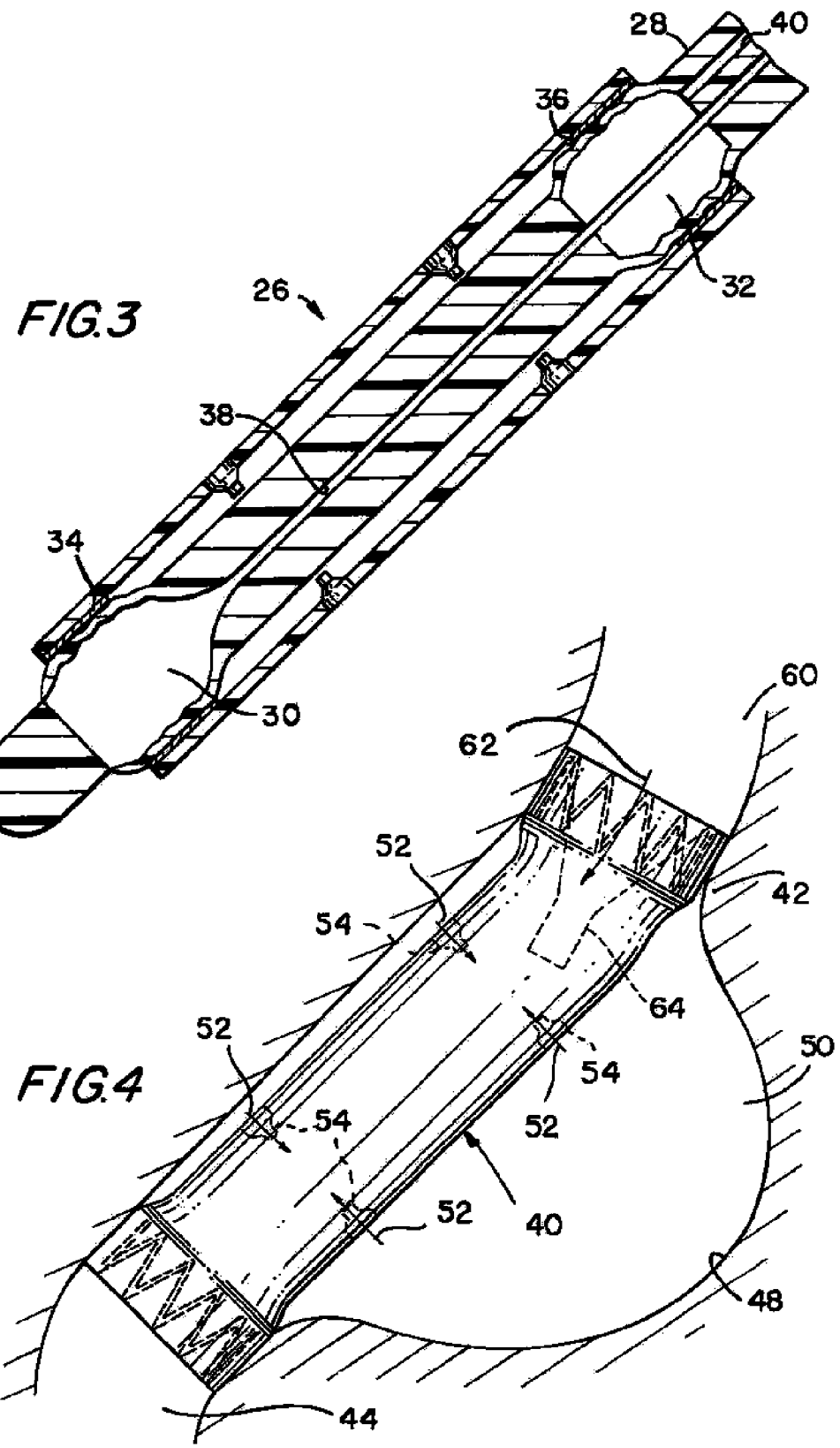

ENDOSCOPIC GASTRIC BYPASS

CROSS-REFERENCE TO RELATED APPLICATION

This application is a continuation of, commonly assigned U.S. patent application Ser. No. 10/229,400, filed Aug. 26, 2002 now U.S. Pat. No. 7,211,114, incorporation herein by reference in its entirety.

FIELD OF THE INVENTION

The invention disclosed herein relates to a method and device for treating obesity. More particularly, the invention relates to a method and device wherein a covered stent having at least one one-way valve is positioned to extend from a patient's gastro-esophageal junction to the patient's duodenum.

BACKGROUND OF THE INVENTION

Surgical treatment of morbid obesity dates back to 1954 when the first jejunoileal bypass (intestinal) was done specifically for weight loss. The premise of this bypass was that patients could eat large amounts of food and the excess would either be poorly digested or passed along too rapidly for the body to absorb excess calories. In addition, intestinal bypass caused a temporary decrease in appetite which also resulted in weight loss. Unfortunately, essential nutrients were also lost in the stool. Because the effects of intestinal bypass were too difficult to predict and manage, the original form of the operation is no longer performed.

In 1969 it was noted that near-total removal of the stomach for cancer or ulcers caused patients to remain at below normal weight. This suggested that a gastric bypass could be used for severe obesity. This approach involved stapling off most of the stomach, bypassing the duodenum, and allowing the undigested food to pass along directly into the intestine. Most of the early operations eventually failed because the pouch became enlarged.

Today there are two primary surgical procedures used for achieving weight loss. One is the vertical banded gastroplasty, commonly referred to as VBG, and the other is the Roux-en-Y gastric bypass, or simply, the gastric bypass.

Gastric bypass involves significant enough risk to a patient that it is considered only as a lifesaving undertaking for morbidly obese individuals. Reported complications following the gastric bypass include postoperative complications and side effects such as marginal ulcers, wound infections, pulmonary emboli, gastrointestinal hemorrhage, renal failure, and numerous other disorders. The nature, severity, and frequency of these problems have in fact led some to doubt the advisability of the known surgical techniques for treatment of obesity. There has been, and continues to be, a need for less traumatic surgical or non-surgical techniques to treat obesity.

OBJECTS OF THE INVENTION

It is an object of the invention to provide a method and device for treating obesity.

It is also an object of the invention to provide an endoscopic device to separate ingested food and gastric fluids.

It is a further object of the invention to provide an endoscopic device to separate ingested food in the small bowel from digestive enzymes.

It is additionally an object of the invention to provide a covered stent having one-way valves.

It is a yet further object of the invention to provide a method for treating obesity wherein a covered stent having one-way valves is inserted into a patient's gastrointestinal tract.

These and other objects of the invention will become more apparent from the discussion below.

SUMMARY OF THE INVENTION

According to the invention, a device is inserted into a patient's stomach endoscopically to separate ingested food from gastric fluids and, optionally, to separate ingested food in the duodenum from digestive enzymes. In one embodiment of the invention, a stent is inserted into a patient's gastrointestinal tract to bypass the stomach. The stent comprises a covered stent having one-way openings and/or valves on its annular surface and preferably at least one one-way valve at one end to permit entry of food and/or liquids. Optionally the one-way valve at the end of the stent can comprise a sleeve that extends through the stent, preferably into the duodenum or beyond. One end of the stent is intended to be positioned at or above the gastro-esophageal junction, and the other end is intended to be positioned in the duodenum or beyond. The net effect of endoscopic gastric bypass is to replicate some or all of the effects of a surgical gastric bypass.

The stent is advantageously delivered on a balloon dilatation catheter having one or more dilatable balloons. Preferably the distal and proximal portions of the stent are attached or crimped to corresponding portions of the catheter, and then, when the stent is properly positioned, balloons are dilated to expand the stent portions. Self-expanding stents, with appropriate catheter-based delivery systems, could be used as well. The stent can be removed by use of one or more of known methods or devices.

BRIEF DESCRIPTION OF THE DRAWINGS

FIG. 3 is a cross-sectional view of an embodiment of the invention on a delivery catheter; and FIG. 4 is a partly cross-sectional view of an embodiment of the invention in position in a patient.

DETAILED DESCRIPTION OF THE INVENTION

Figure 1:
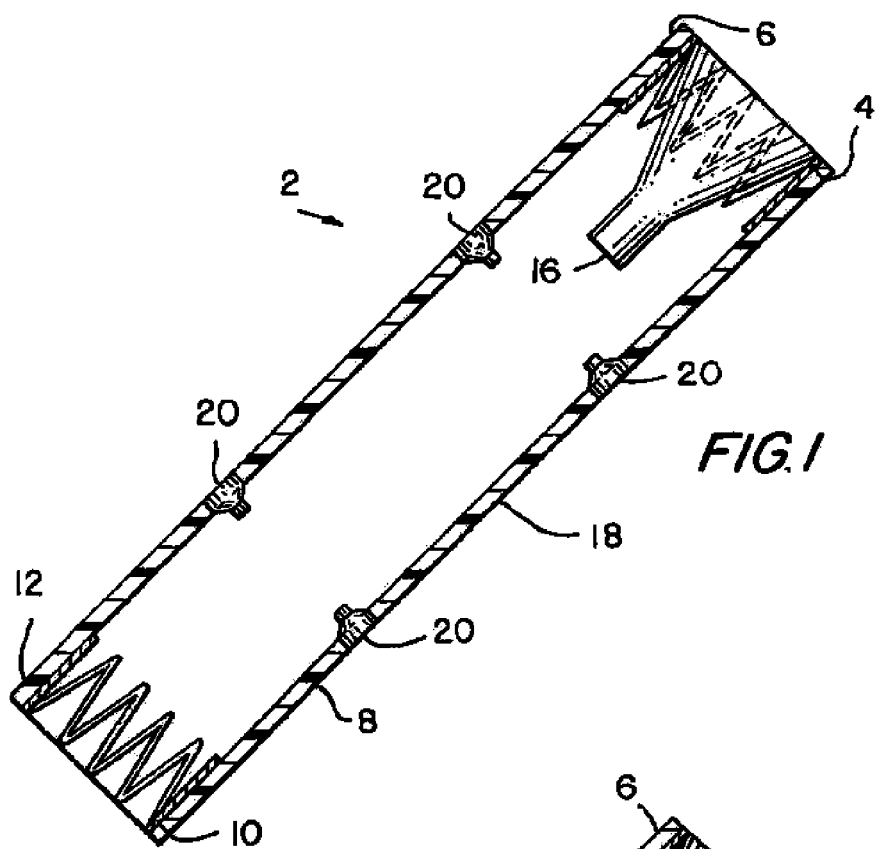
FIG. 1 is a partly cross-sectional view of an embodiment of the invention.

The invention can perhaps be better appreciated by making reference to the drawings. In FIG. 1, a gastric bypass stent 2 comprises a stent member 4 at the proximal end 6 of a tabular member 8 and, optionally, a stent member 10 at the distal end 12 of tubular member 8. Proximal tubular end 6 comprises a one-way valve member 16 to permit passage of food and liquid, and the wall 18 of tubular member 8 comprises one-way openings or valves 20 to permit gastric acid or fluid to flow into stent 2.

Optionally stent 2 could comprise one or more stent members 4, 10 that would together define a lumen and would have a coating or surface that would be the functional equivalent of tubular member 8.

Figure 2:
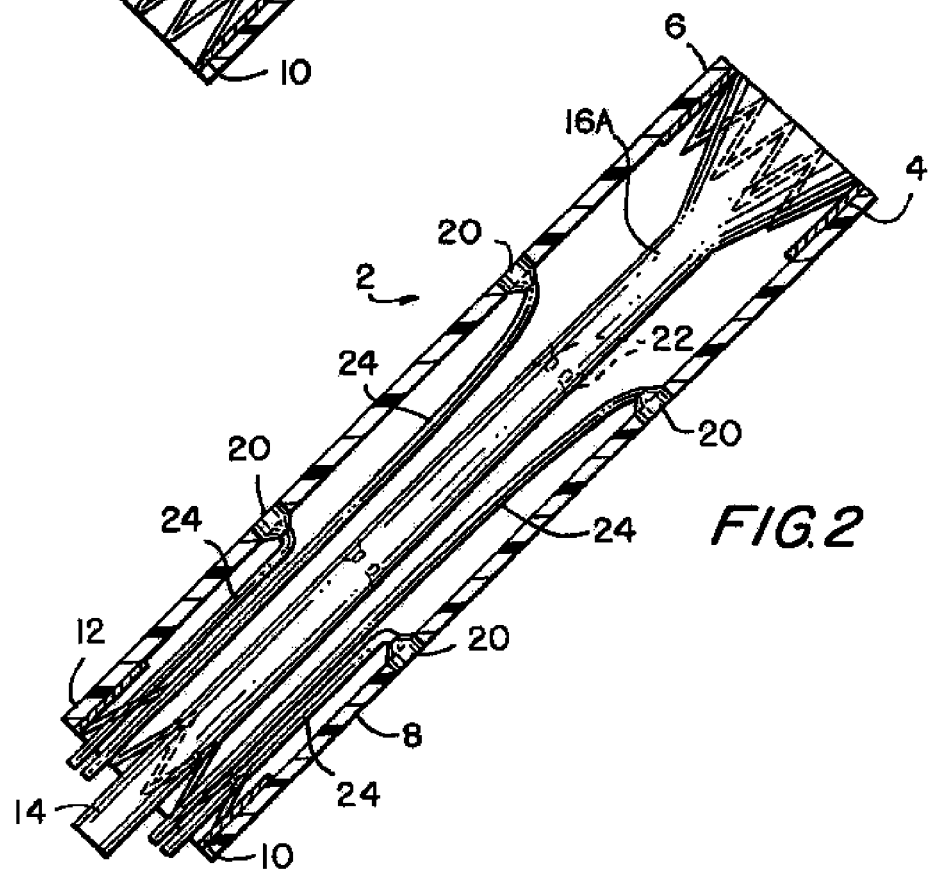
FIG. 2 is a partly cross-sectional view of another embodiment of the invention.

Also, as shown in FIG. 2 the distal portion 14 of valve member 16A may optionally extend to or trough tubular member distal end 12, whereby food from a patient's esophagus (not shown), i.e., ingested food, would not be contacted by gastric acid or fluid within stent 2 or by digestive enzymes within the duodenum (not shown). If it were desired to have some food contact some gastric acid or fluid or digestive enzymes within a distally extending valve member distal portion 14, valve member distal portion 14 could have some one-way valves 22, dependent upon the amount of contact desired. It is within the scope of the invention that valve member distal portion 14 could extend as far as up to about 75% of the small bowel, preferably from about 25 to about 250 cm into the duodenum or beyond.

It is within the scope of the invention that one-way valves 20 could be in fluid connection with tubes 24 that would extend distally to a point substantially near or distal to distal end 12.

One skilled in the art would appreciate the various aspects of the stent of the invention, e.g., the length of valve member 16, the number and position of one-way valves 20 and 22, and the use of tubing 24 connected to valves 20, can be varied to achieve a desired result in terms of when ingested food is contacted by gastric fluid and to what extent.

FIG. 3 is a cross-sectional view of a stent 26 on a delivery catheter 28. Catheter 28 comprises annular dilatation balloons 30 and 32 to expand stent members 34 and 36 once stent 26 is in position within a patient. Balloons 30 and 32 are inflated either sequentially or simultaneously through inflation lumens 38 and 40 to cause stent members 34 and 36 to expand to hold stent 26 in the desired position. Then, balloons 30 and 32 are deflated and catheter 28 is withdrawn.

In FIG. 4 a stent 40 is shown in position, extending from a patient's gastro-esophageal junction 42 to the patient's duodenum 44. Gastric juices generated in the lining 48 of the stomach 50 flow in the direction of arrows 52 through one-way valves 54 into stent 40 and then into duodenum 44. Food or liquids from the esophagus 60 move in direction of arrow 62 through one-way valve 64 into stent 40 and then into duodenum 44, without direct contact with stomach 46.

The width, length, and other parameters of the stent of the invention will vary, especially according to the patient, as one skilled in the art would appreciate. The overall length of the stent will be from about 10 to about 40 cm, preferably from about 12 to about 30 cm, and the expanded diameter will be from about 1.5 to about 4 cm, preferably from about 2 to about 3 cm. The number and placement of one-way valves in each of the stent tubular member 8 or distally extending valve member 16 will vary from 1 to about 50, preferably from about 4 to about 40. The actual number will depend upon factors such as the size of each valve, the overall length of the stent member or valve member, the volume of fluid expected, etc.

Materials useful according to the inventor include biocompatible material such as stainless steel or nitinol and acid resistant polymers.

It will be further apparent to one skilled in this art that the improvements provided for in the present invention, while described with relation to certain specific physical embodiments also lend themselves to being applied in other physical arrangements not specifically provided for herein, which are nonetheless with the spirit and scope of the invention taught here.

We claim:

1. A gastrointestinal implant for insertion into a patient for bypassing a stomach of the patient, the implant comprising:
   a tube with a tube wall adapted to be anchored within the gastrointestinal tract and extending through the stomach; and
   one or more one-way lateral valves in the tube for permitting gastric fluid to flow into a lumen of the tube,
   wherein the one-way lateral valves have valve walls and are configured and oriented at non-zero angles to the tube wall, the valve walls and tube wall having separate non-overlapping annular cross-sections.

2. The gastrointestinal implant of claim 1, wherein the tube is within a tubular member, the tube and tubular member having separate annular walls with an annular space therebetween.

3. The gastrointestinal implant of claim 2, wherein the tubular member has one or more lateral valves.

4. The gastrointestinal implant of claim 1, wherein the tube is a valve.

5. The gastrointestinal implant of claim 1, further comprising at least one of a first stent member positioned at the proximal end of the tube and adapted to engage the gastroesophageal region of the patient and a second stent member positioned at the distal end of the tube and adapted to engage the duodenum of the patient.

6. The gastrointestinal implant of claim 1, wherein the lateral valves are nipple shaped structures extending into the lumen of the tube.

7. A gastrointestinal implant for insertion into a patient for bypassing a stomach of the patient, the implant comprising:
   a tube adapted to be anchored within the gastrointestinal tract and extending through the stomach; and
   one or more lateral valves in the tube for permitting gastric fluid to flow into a lumen of the tube;
   wherein the lateral valves of the tube have tubes extending distally to a point at or distal to a distal end of the tube.

8. The implant of claim 7, wherein the tube has a first end with a stent configured to be anchored in the gastroesophageal region of a patient.

9. A gastrointestinal implant for insertion into a patient for bypassing a stomach of the patient, the device comprising:
   a tube defining a lumen, the tube having a proximal end and a distal end;
   a first stent member positioned at the proximal end of the tube, the first stent member adapted to engage the patient's gastroesophageal region; and
   a second stent member positioned at the distal end of the tube, the second stent member adapted to engage the duodenum of the patient,
   wherein the tube includes a first tubular portion and a valve with a second tubular portion having a full annular section lying within an annular cross section of the first tubular portion and extending along an axis of the first tubular portion, the axis extending between the proximal and distal tube ends, and
   wherein the first tubular portion has one or more lateral valves.

10. The gastrointestinal implant of claim 9, wherein the tube is within a tubular member.

11. The gastrointestinal implant of claim 10, wherein the tubular member has one or more lateral valves.

12. The gastrointestinal implant of claim 11, wherein the tubular member has an annular wall and the one or more lateral valves have annular walls that are separate from the tubular member annular wall.

13. The gastrointestinal implant of claim 9, wherein the valve extends into the intestine.

14. A gastrointestinal implant for insertion into a patient, the implant comprising:
   a tube having a continuous wall defining a lumen, the tube having a first end and a second end;
   a first stent member disposed at the first end of the tube;
   a second stent member disposed at the second end of the tube; and one or more lateral valves in the continuous wall of the tube configured to permit gastric fluid to flow into the lumen of the tube;

wherein the first stent member is adapted to engage the patient's gastroesophageal region;

wherein the second stent member is adapted to engage the patient's duodenum; and wherein the first end of the tube has a one-way valve that extends through the first stent member forming a separate annular structure lying within the tube.

15. The gastrointestinal implant of claim 14, wherein the first and second stent members lie within the continuous wall.

16. The gastrointestinal implant of claim 14, wherein the one-way valve includes a tubular structure that extends coaxially with the tube to the tube second end.

17. The gastrointestinal implant of claim 14, wherein the lateral valves have extended channels configured to convey gastric fluid directly from the patient's stomach to the patient's duodenum.

18. The gastrointestinal implant of claim 17, wherein the lateral valves are one-way valves.

19. A gastrointestinal implant for insertion into a patient, the implant comprising:

a tube with first and second ends and an annular surface and a lumen defined therewithin;

the tube having a one-way valve at the first end thereof to permit entry of food and/or liquids into the lumen;

the annular surface having openings, separate from the one-way valve, to permit gastric fluid to enter the lumen;

the one-way valve having a portion of progressively decreasing internal diameter and a tubular extension that extends lengthwise along the lumen.

20. The gastrointestinal implant of claim 19, wherein the one-way valve includes a sleeve that extends through the tube such that food and/or liquids entering at the first end are conveyed at least partly through the lumen.

21. The gastrointestinal implant of claim 20, wherein the sleeve extends at least to the second end of the tube.

22. The implant of claim 21, wherein the tube includes a one way valve at the tube first end.

* * * * *